US010258739B2

(12) United States Patent
Cefai

(10) Patent No.: US 10,258,739 B2
(45) Date of Patent: Apr. 16, 2019

(54) MECHANICAL DRIVER

(71) Applicant: ViCentra B.V., Utrecht (NL)

(72) Inventor: Joseph John Cefai, West Glamorgan (GB)

(73) Assignee: ViCentra B.V., Utrecht (NL)

( * ) Notice: Subject to any disclaimer, the term of this patent is extended or adjusted under 35 U.S.C. 154(b) by 141 days.

(21) Appl. No.: 15/359,914

(22) Filed: Nov. 23, 2016

(65) Prior Publication Data

US 2017/0072137 A1   Mar. 16, 2017

Related U.S. Application Data

(62) Division of application No. 14/388,661, filed as application No. PCT/NL2013/050227 on Mar. 27, 2013, now Pat. No. 9,987,418.

(30) Foreign Application Priority Data

Mar. 28, 2012   (GB) .................. 1205459.9

(51) Int. Cl.
*F03G 7/06* (2006.01)
*F04B 9/02* (2006.01)
(Continued)

(52) U.S. Cl.
CPC ........ *A61M 5/1452* (2013.01); *A61M 5/1454* (2013.01); *F03G 7/065* (2013.01);
(Continued)

(58) Field of Classification Search
CPC . A61M 5/1452; A61M 5/1454; F04B 19/006; F04B 43/043; F04B 9/02; F03G 7/06
See application file for complete search history.

(56) References Cited

U.S. PATENT DOCUMENTS

2003/0198558 A1   10/2003   Nason et al.
2005/0107811 A1*  5/2005   Starksen .......... A61B 17/00234
                                                    606/143
(Continued)

FOREIGN PATENT DOCUMENTS

CN    2138228 Y    7/1993
CN    1522347 A    8/2004
(Continued)

OTHER PUBLICATIONS

Jul. 11, 2012 Search Report for GB 1205459.9.
(Continued)

*Primary Examiner* — Edelmira Bosques
(74) *Attorney, Agent, or Firm* — Hahn Loeser & Parks, LLP

(57) ABSTRACT

A mechanical driver comprising a wedge shaped member operatively coupled to a shape memory alloy such that the shape memory alloy is able to displace the wedge shaped member in an essentially linear direction. The wedge shaped member is in constant contact with a lever arranged so that it can rotate about a fixed pivot point. A piston is arranged such that it is constant contact with the lever at a point between the pivot point of the lever and the contact point between the lever and the wedge shaped member. Activation of the shape memory alloy displaces the wedge shaped member along its linear direction and this causes the lever to be deflected about its pivot point and the piston to be deflected in an essentially linear direction that is perpendicular to the linear direction of travel of the wedge shaped member.

22 Claims, 10 Drawing Sheets

(51) Int. Cl.
  *A61M 5/145* (2006.01)
  *F04B 19/00* (2006.01)
  *F04B 43/04* (2006.01)
  *F04B 17/00* (2006.01)

(52) U.S. Cl.
  CPC ............... *F04B 9/02* (2013.01); *F04B 17/00* (2013.01); *F04B 19/006* (2013.01); *F04B 43/043* (2013.01); *A61M 2005/14506* (2013.01); *A61M 2205/0244* (2013.01); *A61M 2205/0266* (2013.01); *A61M 2207/00* (2013.01)

(56) References Cited

U.S. PATENT DOCUMENTS

2009/0139727 A1    6/2009  Tanju et al.
2009/0320463 A1*  12/2009  Jansen ................. A47C 21/006
                                                         60/527

FOREIGN PATENT DOCUMENTS

| CN | 1718289 A | 1/2006 |
|----|-----------|--------|
| DE | 10219750 C1 | 7/2003 |
| EP | 2000718 A1 | 12/2008 |
| RU | 2055194 C1 | 2/1996 |
| SU | 1423783 A1 | 9/1988 |
| WO | WO2009118553 A1 | 10/2009 |

OTHER PUBLICATIONS

Nov. 28, 2014 International Search Report for PCT/NL2013/050227.
Dec. 9, 2014 International Preliminary Report on Patentability for PCT/NL2013/050227.
Mar. 15, 2016 Office Communication in connection with CN 2013 800 27523.9.
Oct. 18, 2016 Office Communciation in connection with RU 2014 143 197/06 (069768).

* cited by examiner

MECHANICAL DRIVER

The present application is a divisional of U.S. Ser. No. 14/388,661, which is a § 371 submission of international application no. PCT/NL2013/050227, filed 27 Mar. 2013 and published in the English language on 3 Oct. 2013 with publication no. WO 2013/147602, which claims the benefit of the filing date of GB 1205459.9 filed 28 Mar. 2012.

BACKGROUND

This invention relates to a mechanical driver. Said mechanical driver can be miniature mechanical driver and is often used in a micro-pump. The micro-pump can be used as the fluid pumping device of a drug delivery system.

A variety of mechanical drivers have been described for providing the mechanical displacement required in devices designed for pumping fluids. Examples of these mechanical drivers include devices operating on thermo-pneumatic (U.S. Pat. Nos. 4,265,600 and 6,520,753), electrostatic (U.S. Pat. Nos. 6,168,395 and 5,362,213), piezo electric (U.S. Pat. Nos. 4,596,575 and 6,827,559), thermo-hydraulic (GB2443261), bimetallic (U.S. Pat. No. 5,611,676), stepper motors (EP2072072) and magnetic (U.S. Pat. Nos. 3,819,305 and 7,922,462) mechanical driving principles.

A number of limitations exist with these mechanical driving principles when incorporated into micro-pump designs. A number of these mechanical drivers a too complex and lead to difficulties when designing a product where large numbers need to be manufactured, that are manufactured at high throughput and where the manufacturing process is required to deliver product at a cost effective price. The complexity also limits the design opportunities when they are incorporated into micro-pumps. Other limitations are that the components required in some of the mechanical drivers described above result in a product that is too costly or difficult to manufacture. Yet another limitation is that the materials required when incorporating at least some of the mechanical drivers mentioned above into micro-pump products reduce the opportunities for using the product. As an example, some materials are not compatible with the fluid media that the product is required to pump, because it degrades the commercially important components in the media. This could include commercially important components such as bioactive materials. Yet in other instances, some of the mechanical driving principles are not able to provide the accuracy required for micro-pumps required for drug delivery and other commercially important components. And yet another limitation is that some of the above mechanical driving principles are not able to provide the repeatability required by certain drug delivery products. By way of example, products designed for short term use and that are replaced on a frequent basis require driving principles that can provide repeatable performance across a large number of similar devices. And yet another limitation is that some of the above mechanical driving principles do not provide the power required by the drug delivery device when the mechanical driver is miniaturised.

Shape memory alloy (SMA) has been proposed as a suitable material for a mechanical driver of the type described above and a number of devices based on this mechanical driver have been described. SMA mechanical drivers can be suitable for micro-pump applications due to their high force-to-weight ratio, mechanical simplicity, compactness, and silent, clean operation. SMA mechanical drivers also provide cost effective solutions for the design of short term use, disposable products that are easy to manufacture, that are produced in very large numbers and at a cost effective price.

However, SMA mechanical drivers have disadvantages that limit their use in applications that require high accuracy. One disadvantage of using SMA in these devices is that it has a prominent strain hysteresis and its phase transition is dependent on temperature, stress, the direction of motion, and many other factors (J. D. Harrison, "Measurable Change Concomitant with SME Transformation," *Engineering Aspects of SMAs*, eds. Duering et al., Butterworth, pp 106-209, 1990).

Nonlinear control approaches have been used to compensate for the non-mechanical non-linearity of shape memory alloys. These approaches have included various approaches to controlling the mechanical movement of shape memory alloys such as: neural networks and a sliding mode based robust controller (Song, "Precision tracking control of shape memory alloy actuators using neural networks and a sliding-mode based robust controller," *Smart Mater. Struct.* 12, pp. 223-231, 2003), neural fuzzy (Kumagai, "Neuro-fuzzy model based feedback controller for shape memory alloy actuators," Proceedings of SPIE, v 3984, pp. 291-9, 2000) dissipativity (Gorbet, "Dissipativity approach to stability of a shape memory alloy position control system," *IEEE Transactions on Control Systems Technology*, v 6, n 4, pp. 554-562, July 1998), variable structure control (Grant, "Variable structure control of shape memory alloy actuators," *IEEE Control Systems Magazine*, v 17, n 3, pp. 80-88, June 1997), and pulse width modulation of the actuation energy (NMa and G Song, "Control of shape memory alloy actuator using pulse width modulation," *Smart Mater. Struct.* 12, pp. 712-719, 2003). Despite these often complex approaches to shape memory alloy control, the control of SMA is still difficult.

Several approaches have also been proposed to generate the accuracy of movement required from SMA mechanical drivers by mechanically limiting the range of movement that the SMA can perform. EP2290238A1 describes a device that limits the range of movement of a plunger in a fluid delivery device by proving mechanical stops for both the start and end of the plunger travel. U.S. Pat. No. 7,232,423 describes a device that also uses mechanical stops to accurately define the range of movement created by the SMA mechanical driver. A limitation of these inventions is that these mechanical stops impart strain on the SMA and limit the performance of the driver and could also lead to failure. U.S. Pat. No. 8,047,812 describes a device that aims to reduce the effect of unwanted strain on the SMA by introducing a second piston coupled to the shape memory element that moves to accommodate changes in the shape memory element and reduce stress on the pumping system. By introducing the second piston, this invention increases the complexity of the device, making it more difficult to manufacture and less cost effective. U.S. Pat. No. 8,029,245 describes a device that relies on monitoring the position of the piston in the pumping system and then modulating the energy supplied to the SMA to provide the accuracy required. The requirement for monitoring the position of the plunger in this invention introduces the need for complex sensor and control systems that complicate the design and operation of the device. These added complications also increase the cost and complexity of manufacturing the device. U.S. Pat. No. 6,656,158 describes a fluid dispensing device that uses a SMA to move a pawl against a toothed gear system attached to the fluid dispensing portion of the device. Every time the SMA is activated the pawl moves against the gear and indexes the gear from its first position to a second position. The gear does not return to its first position. This device overcomes the lack of accuracy in the use of SMA, by using the SMA to move an accurately formed gear system. U.S. Pat. No. 6,375,638 describes a device that is similar to the one described in U.S. Pat. No. 6,656,158. U.S. Pat. No. 6,375,638 describes a device where the SMA is used to move a part that then deflects a second part from its first position to a second position. The part that is moved can either move in a linear motion or an angular motion. It is important to note, that this part does not return to its first position, but indexes along the path of travel every time the SMA is activated. In both U.S. Pat. Nos. 6,656,158 and 6,375,638, the complexity of the device described increases the complexity of the manufacturing process and the cost-effectiveness of the manufactured device.

There is a need for an improved shape memory actuator mechanical driver that provides the required accuracy, reliability, ease of manufacture, cost effectiveness and that is scalable and that can be used to drive the reciprocating piston in a micro pump. These will become apparent in the description of the present invention.

STATEMENT OF INVENTION

The invention relates to a mechanical driver comprising a lever which is rotatable at a fixed rotation point, a wedge shaped member operatively coupled to and in constant contact with the lever at a point at a distance from the fixed rotation point to deflect the lever about the fixed rotation point, a shape memory alloy operatively coupled to the wedge shaped member to move the wedge shaped member such that the wedge shaped member deflects the lever, wherein the shape memory alloy is held at a predetermined tension in its start position, and a piston drive point located on and in constant contact with the lever, at a distance from the fixed rotation point of the lever. Further embodiments of said mechanical driver are defined in the claims 2-27. The mechanical driver can be a miniature mechanical driver.

The invention further relates to a mechanical driver comprising a piston, a wedge shaped member operatively coupled and in constant contact with the piston to deflect the piston, and a shape memory alloy operatively coupled to the wedge shaped member to move the wedge shaped member such that the wedge shaped member deflects the piston, wherein the shape memory alloy is held at a predetermined tension in its start position. Further embodiments of said mechanical driver are defined in the claims 29-46. The mechanical driver can be a miniature mechanical driver.

In a further embodiment of any of the above mechanical drivers according to the invention, the shape memory alloy is arranged to move the wedge shaped member in a linear direction from a first position into a second position.

In a further embodiment of any of the above mechanical drivers according to the invention, the piston and the wedge shaped member are arranged so that when the wedge shaped member moves from its first position to its second position, the piston is displaced along a linear direction from a first position to a second position.

In a further embodiment of any of the above mechanical drivers according to the invention, the direction of the movement of the piston is perpendicular to the direction of the movement of the wedge shaped member. The design of the mechanical driver allows to accurately move a piston in a micro pump.

In a further embodiment of any of the above mechanical drivers according to the invention, the wedge shaped member has an angled surface that is in contact with the piston and that acts to displace the piston when the wedge shaped member moves along its linear direction. The angled surface of the wedge shaped member forms an angle with the linear direction of travel of the wedge shaped member. The angle can be optimised to optimise the displacement of the piston. It will be apparent to those skilled in the art that the angle of the surface and the distance the wedge shaped member moves along its linear direction define the distance the piston is displaced from its first position to its second position. The angle that the angled surface of the wedge shaped member makes with the linear direction of travel of the wedge shaped member and the length of the angled surface can both be defined by the physical dimensions of the wedge shaped member. The advantage of this embodiment of the present invention is that the shape of the wedge shaped member determines the extent and accuracy of displacement of the piston. The angled surface of the wedge shaped member can be further modified to incorporate surfaces that are essentially planar to the direction of travel of the wedge shaped member. One surface can be added to the leading edge of the wedge shaped member and directly preceding the angled surface. The other planar surface can be added directly after the angled surface. The two planar surfaces and the sloping surface can be arranged so that they form a continuous surface. The wedge shaped member can be arranged so that when it is in its first position one end of the piston is in contact with the first planar surface. When the wedge shaped member is displaced along its linear direction of travel the end of the piston travels along the angled surface and is displaced from its first position to its second position. The extent to which the piston is displaced can be defined by the angle of the angled surface and the length of the angled surface. Once the piston reaches the second planar surface at the end of the angled surface it cannot be displaced further. The advantage of the present invention is that the displacement of the piston by the wedge shaped member is not determined by the distance the wedge shaped member travels along its linear direction of travel so long as the first position of the wedge shaped member allows the piston to at least contact a portion of the first planar surface and the second position of the wedge shaped member allows the piston to contact at least a portion of the second planar surface. It will be apparent to those skilled in the art that the shape of the wedge shaped member can be incorporated into other embodiments of the mechanical driver according to the present invention. The above configuration is explained in relation to the mechanical driver wherein the piston in contact with the wedge shaped member. It will be clear that it can be applied in a similar way in the mechanical driver wherein a lever is in contact with the wedge shaped member.

In a further embodiment of any of the above mechanical drivers according to the invention, The lever comprises one end that forms the fixed rotation point and a moveable end that is moveable about the fixed rotation point. The movable end of the lever is arranged so that it is in permanent contact with the wedge shaped member, and that the wedge shaped member is able to slide relative to the movable end of the lever. There is provided a point on the lever, at a distance along the lever between the fixed point of rotation of the lever and the point of contact of the lever with the wedge shaped member, where the lever is in permanent contact with a piston. The piston is arranged such that it can move in a linear direction that is as close as practically possible along a tangent to the angular movement of the lever. When the wedge shaped member moves from the first position to the second position it acts to deflect the moveable end of the lever from a first position to a second position. When the lever is deflected to its second position by the wedge shaped member, the lever deflects the piston from a first position to a second position. When the shape memory alloy cools, a return spring can pull the wedge shape member from its second position to its first position, the lever rotates from its second position to its first position, and the piston moves from its second position to its first position. The mechanical driver allows for the accuracy and repeatability of movement of the piston from its first position to its second position to be optimised by accurately defining the wedge shaped member and also by optimising the position of the piston along the lever relative to the fixed point of rotation of the lever and the contact point between the lever and the wedge shaped member. The position on the lever that provides the point of contact with the piston relative to the position of the fixed point of rotation and the contact point between the lever and the wedge shaped member can be optimised to deliver the piston movement and accuracy required.

Current manufacturing technologies such as injection molding of polymer parts can produce plastic parts within a manufacturing tolerance of about +/−20 microns. In some cases, +/−10 microns is possible. It is therefore possible using current injection molding techniques to define the wedge shaped member of this invention to those accuracies. In certain circumstances this provides sufficient piston movement accuracy that is suitable for manufacturing micro-pumps that can be used in drug delivery device capable of accurate drug delivery.

In a further embodiment of any of the above mechanical drivers according to the invention, the wedge shaped member can have two angled surfaces. One surface is coupled to the piston or the lever and the other is coupled to an angled surface at a fixed position. The two angled surfaces of the wedge shaped member are positioned such that they are essentially opposite each other. It will be apparent to those skilled in the art that this arrangement of angled surfaces allows the gradient of the surfaces to be reduced while retaining the deflection caused by the movement of the wedge shaped member.

In a further embodiment of any of the above mechanical drivers according to the invention, the wedge shaped member is arranged so that it cannot rotate about its axis of travel or perpendicular to its axis of travel. This arrangement increases the efficiency of the deflection caused by the wedge shaped member when it moves between its first and second positions.

A In a further embodiment of any of the above mechanical drivers according to the invention, the position of the piston can be arranged at a point along the lever to increase the accuracy of the micro-pump. Positioning the piston on the lever at a point between the contact point between the wedge shaped member and the lever, and the fixed point of rotation of the lever allows the accuracy of the movement of the piston to be optimised.

In a further embodiment of any of the above mechanical drivers according to the invention, the piston is arranged so that as far as is possible its direction of travel is restricted. This arrangement increases the efficiency of the deflection caused by the wedge shaped member or the lever acting on the piston.

In a further embodiment of any of the above mechanical drivers according to the invention, the lever is sufficiently rigid to avoid bending of the lever during the action of the miniature mechanical driver.

In a further embodiment of any of the above mechanical drivers according to the invention, a spring is incorporated to move the lever from its second position to its first position. The spring may be a silicone structure connected to the lever at one end and to a fixed point at the other.

In a further embodiment of any of the above mechanical drivers according to the invention, a spring is incorporated to move the piston from its second position to its first position. The spring may be a silicone structure connected to the piston at one end and to a fixed point at the other.

In a further embodiment of any of the above mechanical drivers according to the invention, the mechanical driver is used to drive the reciprocating piston of a micro-pump for infusing liquid drugs. The pump can comprise a pumping chamber having an inlet and outlet, wherein the volume of the pumping chamber is caused to change by the action of the mechanical driver. Such a pump can be part of a drug delivery device comprising a reservoir of drug maintained at a positive pressure such that when the pumping chamber is filling with liquid drug, the positive pressure of the drug reservoir assists in the filling of the pumping chamber. To prevent unintentional delivery of liquid drug from the drug reservoir, valves are provided at the inlet and outlet to the pumping chamber. The valves can be designed such that the inlet valve allows fluid to enter the pumping chamber from the drug reservoir when the pumping chamber is filling, and the outlet valve only allows fluid to pass through it when the volume of the pumping chamber is reduced by the action of the miniaturised mechanical driver.

In a further embodiment of any of the above mechanical drivers according to the invention, the mechanical driver is formed from parts that are essentially flat and that can be easily stacked together to form the miniaturised mechanical driver. This preferred embodiment of the present invention has the advantage of being relatively simple to manufacture.

In a further embodiment of any of the above mechanical drivers according to the invention, the return springs for the wedge shaped member and the lever are formed from an elastomeric material such as silicone, and formed during the fabrication of the wedge shaped member or the lever.

In a further embodiment of any of the above mechanical drivers according to the invention, the mechanical driver is suitable for a micro-pump with a pumping chamber with a volume of less than 100 micro liters.

INTRODUCTION TO DRAWINGS

The above objects and other advantages of the present invention will become more apparent by describing in detail the preferred embodiments of the present invention with reference to the attached drawings in which.

Figure 16:
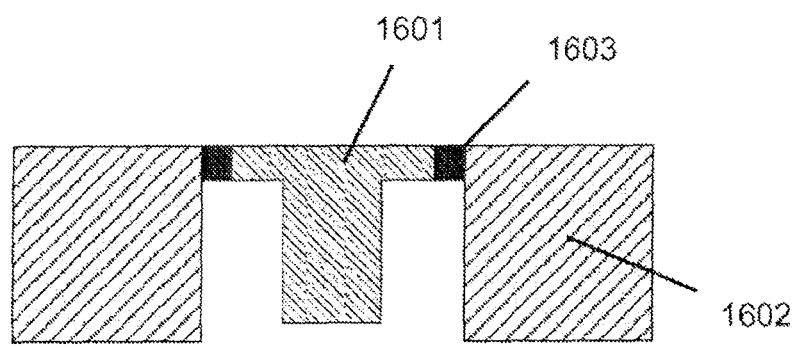
Figure 17:
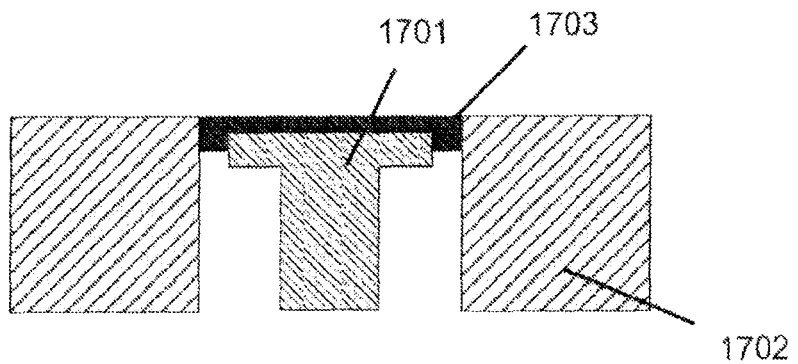
Figure 18:
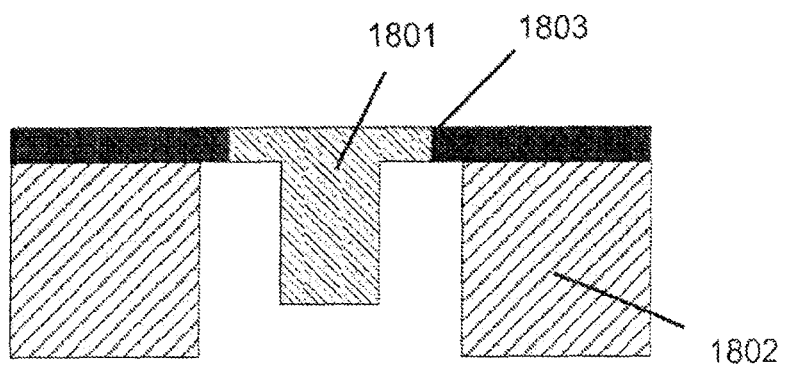
Figure 19:
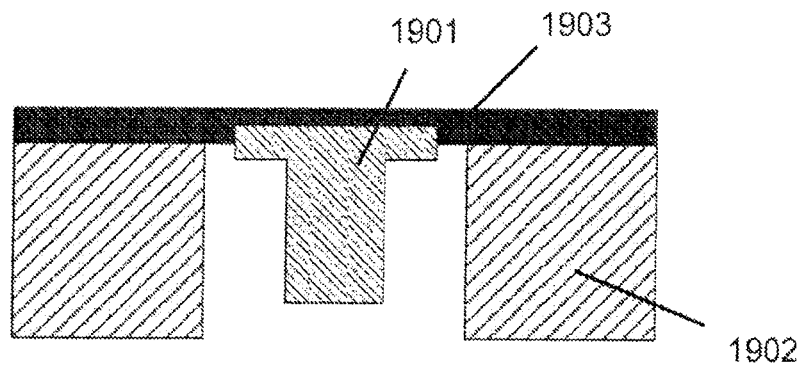
Figure 20:
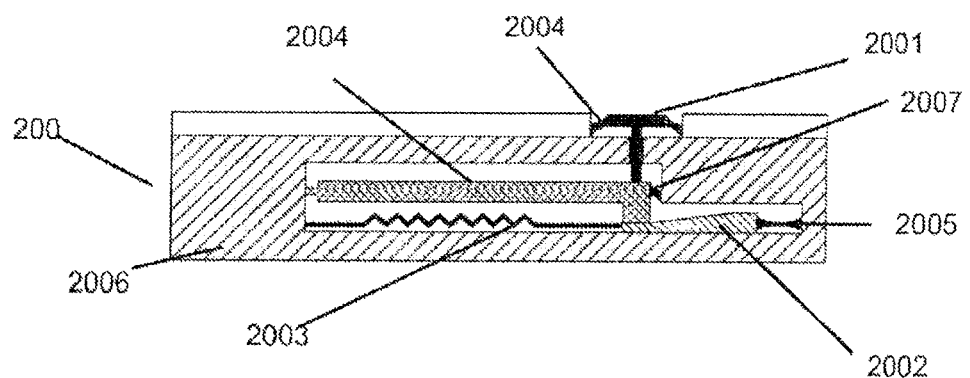
Figure 21:
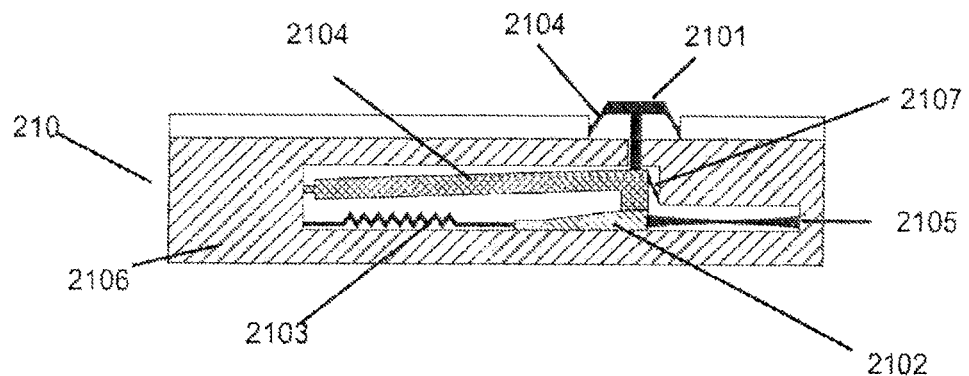

FIG. 16 is a cross section through a first arrangement of the return spring on the piston FIG. 17 is a cross section through a second arrangement of the return spring on the piston FIG. 18 is a cross section through a third arrangement of the return spring on the piston FIG. 19 is a cross section through a fourth arrangement of the return spring on the piston FIG. 20 is a cross section through a mechanical driver according to a fifth embodiment of the invention FIG. 21 is a cross section through a mechanical driver according to a fifth embodiment of the invention showing the shape memory alloy wire contracted and the piston deflected to its second position.

Figure 22:
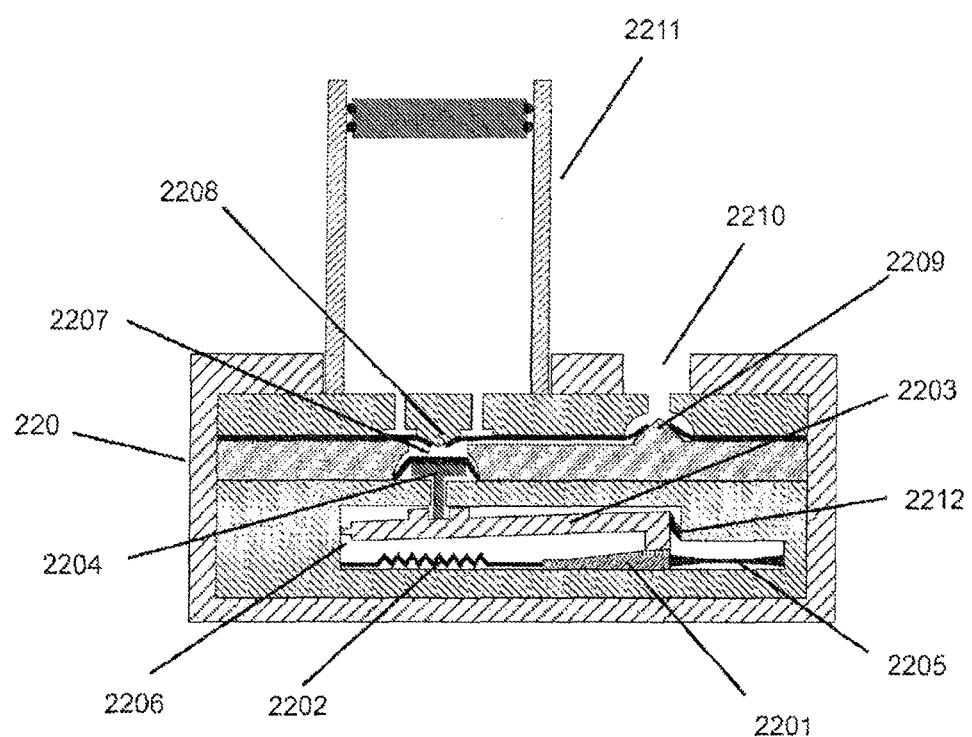

FIG. 22 is a cross section view of a micro pump comprising a mechanical driver according to the present invention.

DETAILED DESCRIPTION

Figure 1:
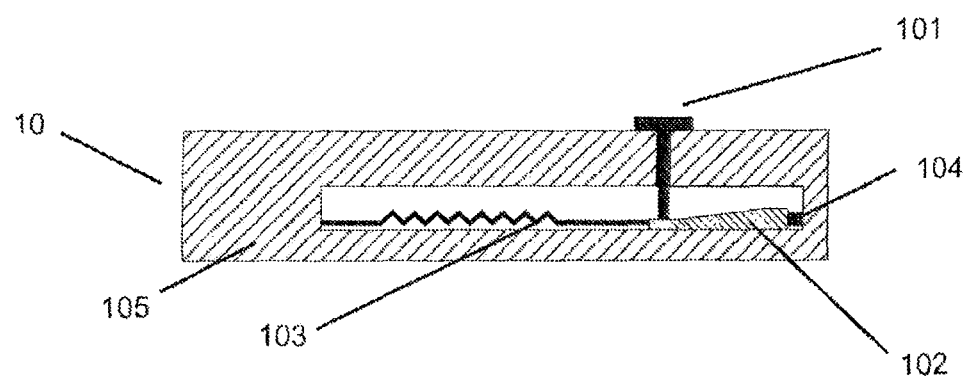
FIG. 1 is a cross section though a mechanical driver according to a first embodiment of the invention.

The first embodiment of the mechanical driver is shown in FIG. 1. The mechanical driver is a miniature mechanical driver. FIG. 1 shows the miniaturised mechanical driver 10 in its non activated state. The miniaturised mechanical driver 10 comprises a wedge shaped member 102. The wedge shaped member 102 is arranged so that it can move in one plane and in an essentially linear direction. The wedge shaped member 102 has at least one angled surface arranged so that it forms an angle with the direction of travel of the wedge shaped member 102. A shape memory actuator 103 is fixed to the wedge shaped member 102 at one end and to the frame 105 of the miniaturised mechanical driver 10. The shape memory actuator 103 is arranged so that it acts along the linear direction of travel of the wedge shaped member 102. The shape memory actuator 103 is also referred to as shape memory alloy. Both terms relate to an actuator made from a shape memory alloy material. A return spring 104 is attached at one end to the wedge shaped member 102 and to the frame 105 of the miniaturised mechanical driver 10 at the other end. The return spring 104 is arranged so that it acts along the linear direction of travel of the wedge shaped member 102. A piston 101 is arranged so that it is in constant contact with the angled surface of the wedge shaped member 102 at one end. The piston 101 is further arranged so that it can move in a direction that is essentially perpendicular to the plane in which the wedge shaped member 102 is arranged to move. FIG. 1 shows the device in the start position with the wedge shaped member 102 and the piston 101 being at their first position (also referred to as their start position), the shape memory alloy 103 in a cooled state and elongated and the return spring 104 contracted.

The shape memory alloy 103 can be in the form of wire formed from a number of shape memory effect metal alloys such as NiTi (Nickel-Titanium), CuZnAl, and CuAlNi. The shape memory alloy can be fixed to the frame 105 and the wedge shaped member 102 using techniques such as crimping or other techniques known to those skilled in the art. In a preferred embodiment the return spring 104 is formed from an elastomeric material such as silicone or rubber. In a preferred embodiment the return spring 104 is formed by injection molding or casting the elastomeric material. In a further preferred embodiment the return spring 104 is formed by casting the elastomeric material and then curing the material with radiation. In a further preferred embodiment the elastomeric material is injection molded or cast in situ and to fix the return spring 104 to the wedge shaped member 102 and to the frame 105. A number of elastomeric materials are suitable for this purpose including self adhesive liquid silicone preparations for injection molding such as Elastosil LR 3071 and Silpuran 6700 (Wacker Chemie AG, München, Germany) and self adhesive liquid silicone preparations for casting and ultra violet light curing such as Loctite Nuva-Sil Silicone (Henkel AG & Co. KGaA, Dusseldorf, Germany) and Novaguard RTV 800-305 (NovaGuard, Clevland, Ohio, USA). It is preffered that the material used in the fabrication of the frame 105 is the same as the material chosen for the wedge shaped member 102. This would simplify the manufacturing process and could allow the manufacture of the wedge shaped member 102 and the frame 105 in a single process such as an injection molding step.

Figure 2:
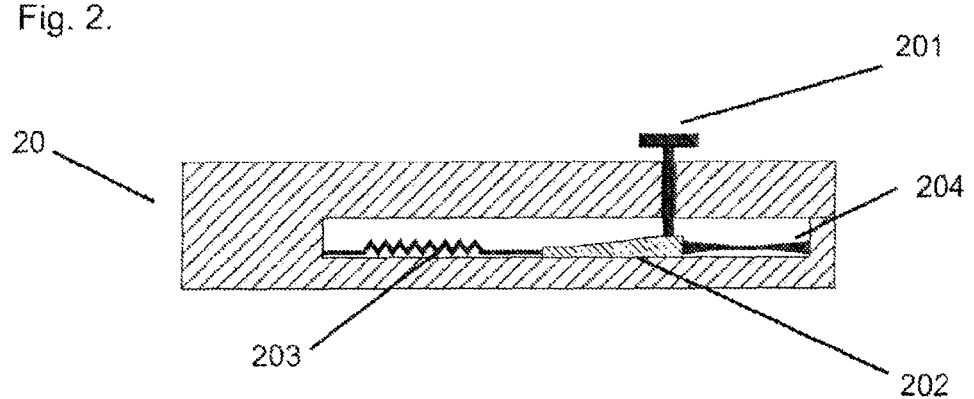
FIG. 2 is a cross section through a mechanical driver according to a first embodiment of the invention showing the shape memory alloy wire contracted and the piston deflected to its second position.

FIG. 2 shows the mechanical driver described in FIG. 1 when the mechanical driver has been operated. Operation of the mechanical driver 20 requires that the shape memory alloy 203 is heated, preferably by passing an electric current through it. The shape memory alloy 203 contracts when heated and acts to displace the wedge shaped member 202 to its second position. Displacement of the wedge shape member 202 acts to elongate the return spring 204. Displacement of the wedge shaped member 202 to its second position also acts to displace the piston 201 to its second position and in a linear direction essentially perpendicular to the plane of movement of the wedge shaped member 202. FIG. 2 shows the shaped memory alloy 203 in a contracted state, the wedge shaped member 202 in its second position, the return spring 205 in an elongated state and the piston 201 displaced to its second position.

When the shape memory alloy 203 is allowed to cool or is actively cooled, the shape memory alloy 203 extends. When the shape memory alloy 203 is allowed to cool, the return spring 204 acts to return the wedge shaped member 202 to the first position. When the wedge shaped member 202 returns to its first position the piston 201 returns to its first position. The first positions (also referred to as the start positions) of the wedge shaped member 202 and the piston 201 are the positions shown in FIG. 1 of the wedge shaped member 102 and the piston 101.

Figure 3:
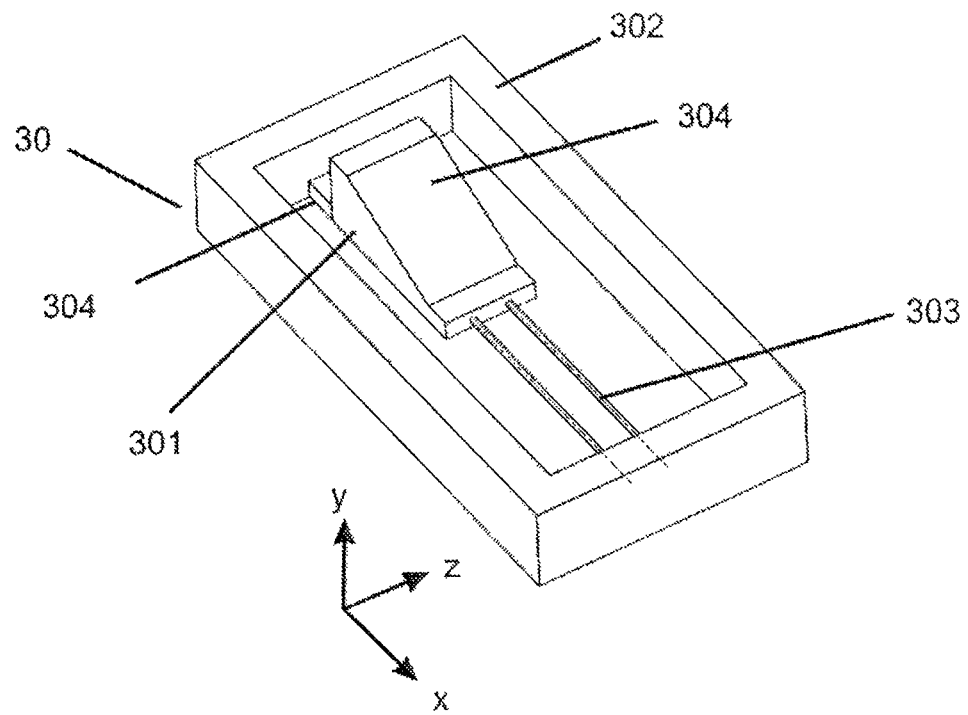
FIG. 3 shows the orientation of the wedge shaped member, shape memory alloy and return spring

FIG. 3 shows a preferred embodiment of the wedge shaped member 301 and the frame 302 of a miniaturised mechanical driver 30 according to this invention. A shape memory alloy 303 is fixed to the wedge shaped member 301 at one end and to the frame 302 at the other end. A return spring 304 is fixed to the wedge shaped member 301 at one end and to the frame 302 at the other end. The wedge shaped member 301 is arranged so that it moves in a linear fashion along the x axis of the miniaturised mechanical driver 30. The wedge shaped member 301 is also preferably arranged so that the angled surface of the wedge shaped member 304 can move along axis x while maintaining a fixed angle with axis z and axis x. In a preferred embodiment the wedge shaped member 301 is arranged so that it cannot rotate about axis x or axis y.

Figure 4:
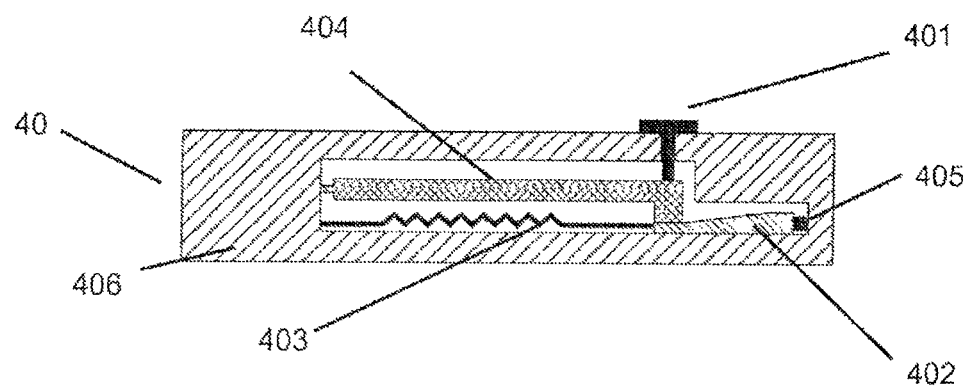
FIG. 4 is a cross section through a mechanical driver according to a second embodiment of the invention

FIG. 4 shows a second embodiment of the mechanical driver according to the present invention substantially identical to the first embodiment of the mechanical driver according to the present invention described with reference to FIGS. 1 and 2 and incorporating a wedge shaped member as described with reference to FIG. 3 except that a lever 404 is included to operatively connect the wedge shaped member 402 to the piston 401. The lever 404 is rotatable at a fixed rotation point. The wedge shaped member 402 is operatively coupled to and in constant contact with the lever 404 at a point at a distance from the fixed rotation point to deflect the lever 404 about the fixed rotation point. A piston drive point is located on and in constant contact with the lever 404, at a distance from the fixed rotation point of the lever 404. The piston 401 is in constant contact with the lever 404 at the piston drive point. It will be appreciated by those skilled in the art that elements of the first embodiment and of the wedge shaped member described with reference to FIG. 3 can be combined in the second embodiment. FIG. 4 shows the second embodiment of the mechanical driver 40 according to the present invention in the start position. The wedge shaped member 402, the lever 404 and the piston 401 are in the first position. The shape memory alloy 403 is elongated and the return spring 405 compressed. The lever 404 is arranged such that it is in constant contact with the wedge shaped member 402. The wedge shaped member 402 is connected to the frame 406 via the return spring 405. The fixed rotation point is also referred to as pivot point. Both terms relate to the fixed point about which the lever 404 in use rotates.

Figure 5:
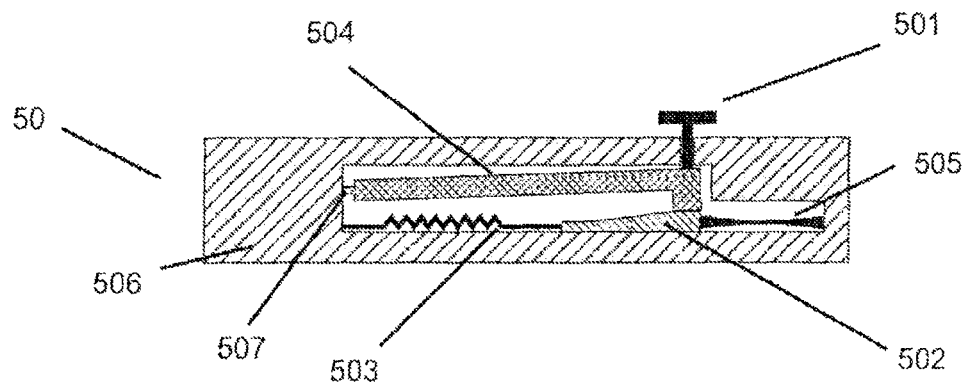
FIG. 5 is a cross section through a mechanical driver according to a second embodiment of the invention showing the shape memory alloy wire contracted and the piston deflected to its second position.

FIG. 5 shows the activated form of the second embodiment of the mechanical driver according to the present invention. The shape memory alloy 503 is heated preferably by passing an electric current through it. The heated shape memory alloy 503 contracts and moves the wedge shaped member 502 from its first position shown in FIG. 4 to its second position shown in FIG. 5. When the wedge shaped member 502 moves from its first position to its second position it elongates the return spring 505. When the wedges shaped member 502 moves from its first position to its second position it also moves the lever 504 from its first position shown in FIG. 4 to its second position shown in FIG. 5. The lever moves in an angular direction about the pivot point 507. When the lever 504 moves to its second position it moves the piston 501 from its first position shown in FIG. 4 to its second position shown in FIG. 5. In the mechanical driver 50, the lever 504 is connected to the frame at the fixed rotation point 507. The piston drive point is also referred to as contact point. Both terms relate to the point on the lever 504 by which the piston 501 is driven to move.

Figure 6:
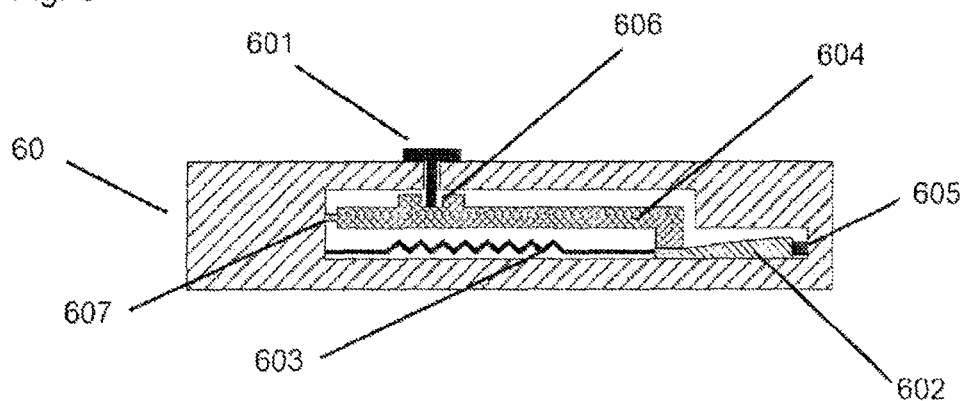
FIG. 6 is a cross section through a mechanical driver according to a third embodiment of the invention

FIG. 6 shows a third embodiment of the mechanical driver according to the present invention that is substantially similar to the second embodiment described in FIGS. 4 and 5 except for the location of the contact point 606 (also referred to as piston drive point) between the piston 601 and the lever 604. The piston 601 is arranged at a point between the pivot point 607 of the lever 604 and the end of the lever in contact with the wedge shaped member 602. The location of the contact point 606 can be fixed relative to the pivot point 607 and the contact point of the lever with the wedges shaped member 602 to optimise the accuracy of the movement of the piston 601. By way of example, an error in moving the lever at the contact point with the wedge shaped member 602 can be reduced by fixing the contact point 606 closer to the pivot point 607. FIG. 6 shows the third embodiment of the mechanical driver 60 according to the present invention in the start position with the wedge shaped member 602, the lever 604 and the piston 601 being at their first position, the shape memory alloy 603 in a cooled state and elongated and the return spring 605 contracted.

Those skilled in the art will appreciate that elements of the wedge shaped member design described in FIG. 3 can be incorporated into the third embodiment of the present invention. Those skilled in the art will also appreciate that elements of the design of the lever described in FIGS. 14 and 15 can also be incorporated into the third embodiment of the mechanical driver according to the present invention.

Figure 7:
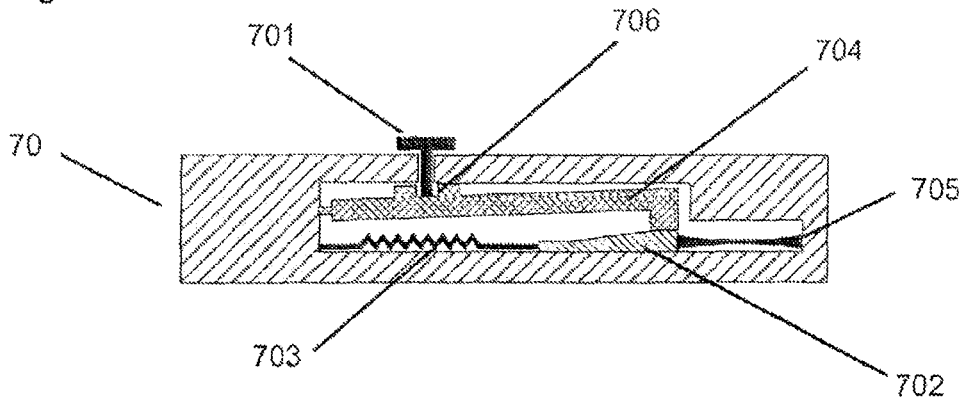
FIG. 7 is a cross section through a mechanical driver according to a third embodiment of the invention showing the shape memory alloy wire contracted and the piston deflected to its second position.

FIG. 7 shows the third embodiment of the mechanical driver according to the present invention in an activated state. Activation of the third embodiment of the mechanical driver according to the present invention is substantially similar to the activation of the second embodiment of the mechanical driver according to the present invention. The wedge shaped member 702, the lever 704 and the piston 701 of the mechanical driver 70 are located in the their second position. FIG. 7 furthermore shows the shape memory alloy 703, the return spring 705 and the piston drive point 706.

Figure 8:
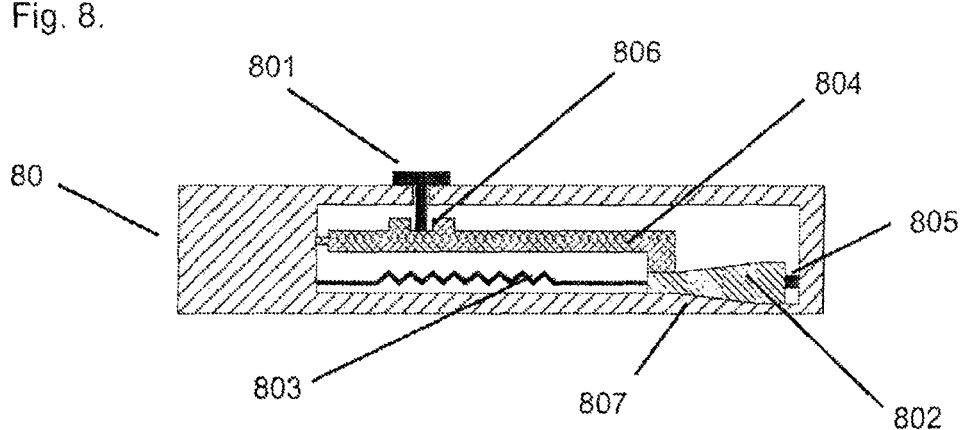
FIG. 8 is a cross section through a mechanical driver according to a fourth embodiment of the invention
Figure 9:
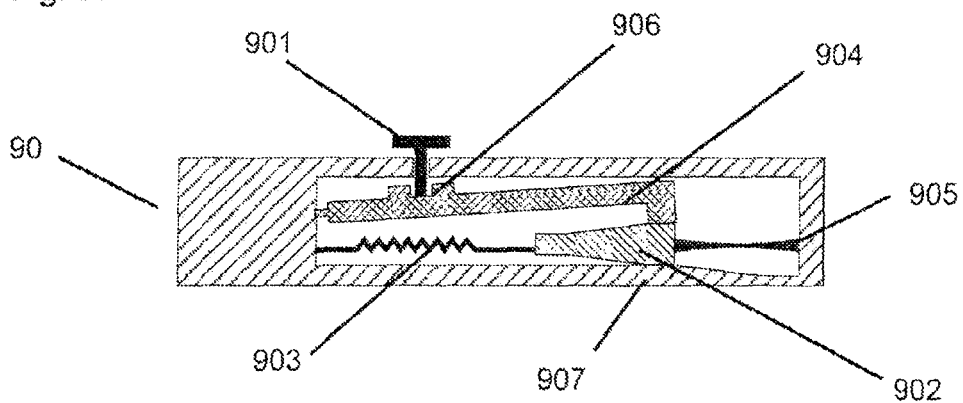
FIG. 9 is a cross section through a mechanical driver according to a fourth embodiment of the invention showing the shape memory alloy wire contracted and the piston deflected to its second position.

FIG. 8 shows a fourth embodiment of the mechanical driver according to the present invention that is substantially similar to the second and third embodiments of the mechanical driver according to the present invention with the exception of the wedge shaped member 802. The wedge shaped member 802 in the fourth embodiment of the mechanical driver according to the present invention has two angled surfaces. The first angled surface is in contact with the lever 804 and the second angled surface is arranged on the opposing surface of the wedge shaped member 804 to the first angled surface. The second angled surface of the wedge shaped member 802 is in contact with the frame 807. The area of the frame 807 that is in contact with the wedge shaped member 802 is also angled to accommodate the angled surface of the wedge shaped member 802. The angled surface of the frame 807 is also arranged such that when the wedge shaped member 802 is moved from its first position to its second position the angled surface of the frame 807 deflects the wedge shaped member towards the lever 804. The activated state of the fourth embodiment of the mechanical driver according to the present invention is described in greater detail in FIG. 9. It will be apparent to those skilled in the art that certain aspects of the wedge shaped member described in FIG. 3 can be incorporated in to the fourth embodiment of the mechanical driver according to the present invention. FIG. 8 shows the fourth embodiment of the mechanical driver according to the present invention in the start position. The wedge shaped member 802, the lever 804 and the piston 801 are in the first position. The shape memory alloy 803 is elongated and the return spring 805 compressed. The lever 804 is arranged such that it is in constant contact with the wedge shaped member 802. FIG. 8 furthermore shows the piston drive point 806 of the lever 804 of the mechanical driver 80. FIG. 9 shows the activated state of the fourth embodiment of the mechanical driver according to the present invention. The shape memory alloy 903 is heated preferably by passing an electric current through it. The heated shape memory alloy 903 contracts and moves the wedge shaped member 902 from its first position shown in FIG. 8 to its second position shown in FIG. 9. When the wedge shaped member 902 moves from its first position to its second position it elongates the return spring 905. When the wedge shaped member 902 moves from its first position to its second position it moves along the angled surface of the frame 907 such that the angled surface of the frame 907 and the angled surface of the wedge shaped member 902 act cooperatively to displace the wedge shaped member 902 towards the lever 904.

When the wedge shaped member 902 moves from its first position to its second position it moves the lever 904 from its first position shown in FIG. 8 to its second position shown in FIG. 9. When the lever 904 moves to its second position it moves the piston 901 from its first position shown in FIG. 8 to its second position shown in FIG. 9. FIG. 9 furthermore shows the piston 901 and the piston drive point 906 of the lever 904 of the mechanical driver 90. The fourth embodiment of the mechanical driver according to the present invention has the advantage of increasing the distance the wedge shaped member is able to displace the lever and the piston for a given length of contraction by the shaped memory alloy without an increase in the angle of the angled surface.

It will be appreciated by those skilled in the art that the wedge shaped member and the frame described in the fourth embodiment of the mechanical driver according to the present invention can be incorporated into the first and second embodiments of the mechanical driver according to the present invention.

Figure 10:
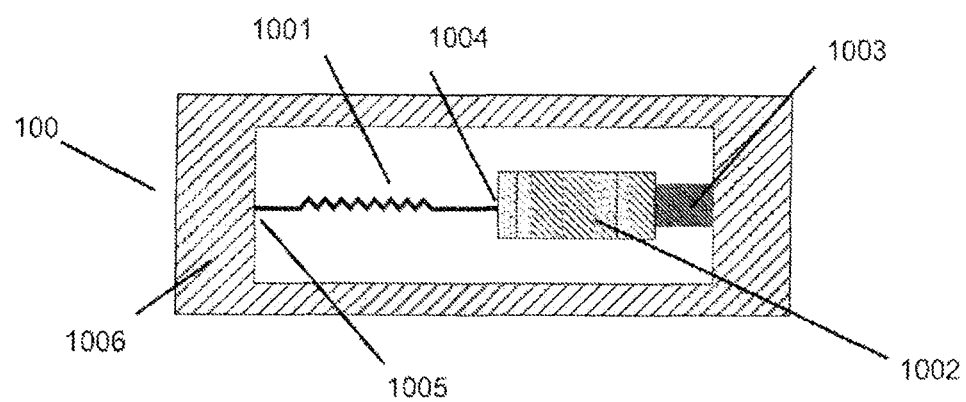
FIG. 10 is a plan view of a first embodiment of the wedge shaped member, the shape memory alloy and the return spring of a mechanical driver according to the present invention.
Figure 11:
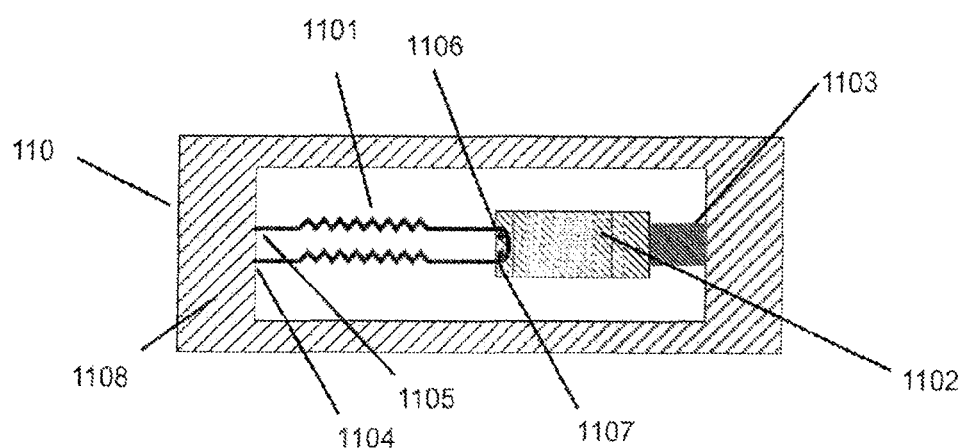
FIG. 11 is a plan view of a second embodiment of the wedge shaped member, the shape memory alloy and the return spring of a mechanical driver according to the present invention.
Figure 12:
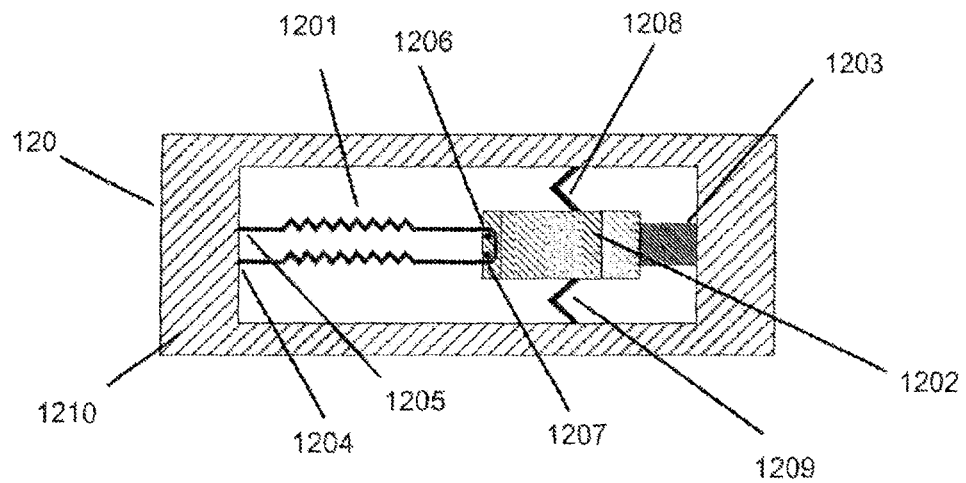
FIG. 12 is a plan view of a third embodiment of the wedge shaped member, the shape memory alloy and the return spring of a mechanical driver according to the present invention.
Figure 13:
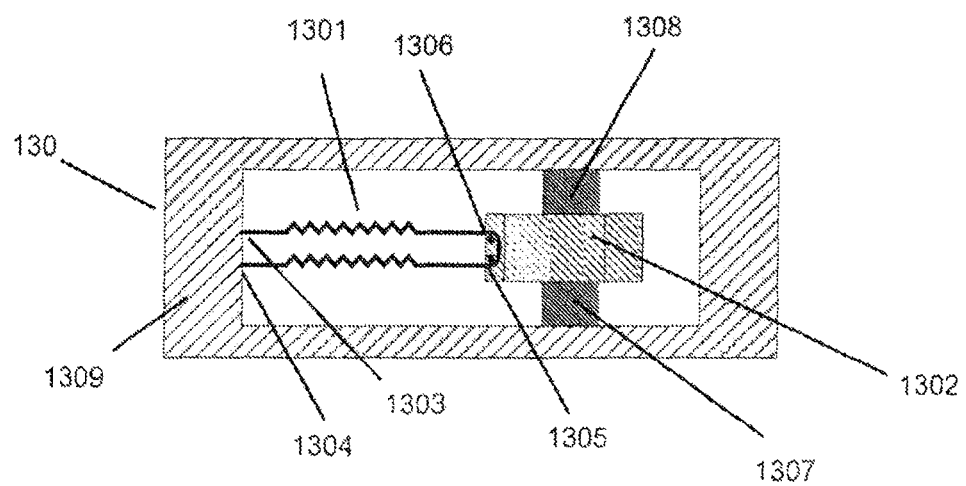
FIG. 13 is a plan view of a fourth embodiment of the wedge shaped member, the shape memory alloy and the return spring of a mechanical driver according to the present invention.

FIGS. 10, 11, 12 and 13 show alternative arrangements of the wedge shaped member and the shape memory alloy and the return spring. FIG. 10 shows an arrangement of the shape memory allow 1001 fixed at one end to the wedge shaped member 1002 at first fixing point 1004 and to the frame 1006 at second fixing point 1005. FIG. 10 shows an arrangement of the wedge shaped member and the return spring 1003. The return spring 1003 is arranged so that one end is fixed to the frame and the other is fixed to the end of the wedge shaped member 1002 that is opposite to the shape memory alloy fixing point 1004. FIG. 11 shows an alternative arrangement for the shape memory alloy 1101 that is substantially similar to the arrangement shown in FIG. 10 except for the arrangement of the shape memory alloy 1101. The shape memory alloy 1101 is fixed at the first fixing point 1104 to the frame 1108 and at a second fixing point 1105 to the frame 1108. The shape memory alloy 1101 is passed around two members 1106 and 1107 positioned on the wedge shaped member 1102 such that it is free to slide around these members. This arrangement is advantageous in that the electrical connections to the shape memory alloy 1101 can also serve as the fixing points 1104 and 1105. The wedge shaped member 1102 is connected to the frame 1108 via the return spring 1103. FIG. 12 shows an alternative arrangement substantially similar to that shown in FIG. 11 with the addition of a connecting bridge comprising flexible tether members 1208 and 1209 between the wedge shaped member 1202 and the frame 1210. The members 1208 and 1209 are arranged to allow the wedge shaped member 1202 to at least move along its intended plane of movement. The members 1208 and 1209 are advantageous by allowing the wedge shaped member and the frame to be moulded as a single unit. The memory shape alloy 1201 is passed around two members 1206 and 1207 and fixed at the first and second fixing points 1204, 1205. The wedge shaped member 1202 is connected to the frame 1210 via the return spring 1203. Those skilled in the art will appreciate that the features can be combined with the arrangement shown in FIG. 10. FIG. 13 shows an alternative arrangement of the wedge shaped member and the return spring. The return spring 1307 and 1308 is fixed at one end to the frame 1309 and at the other end to a side of the wedge shaped member 1302 other than the side that is opposite to the fixing point of the shape memory alloy 1301. The memory shape alloy 1301 is passed around two members 1306 and 1307 and fixed at the first and second fixing points 1303, 1304. Those skilled in the art will appreciate that certain elements of the arrangement shown in FIG. 13 can be incorporated into the arrangement shown in FIG. 10. It will also be apparent to those skilled in the art that the features described in the arrangement shown in FIG. 12 can be incorporated into the arrangement described in FIG. 13.

The shape memory alloy can be fixed at the fixing points using crimping, soldering or welding. Those skilled in the art will appreciate that other methods exist for fixing the shape memory alloy.

It will be apparent to those skilled in the art that certain aspects of the arrangements shown in FIGS. 10, 11, 12 and 13 can be incorporated into other embodiments of the present invention.

Figure 14:
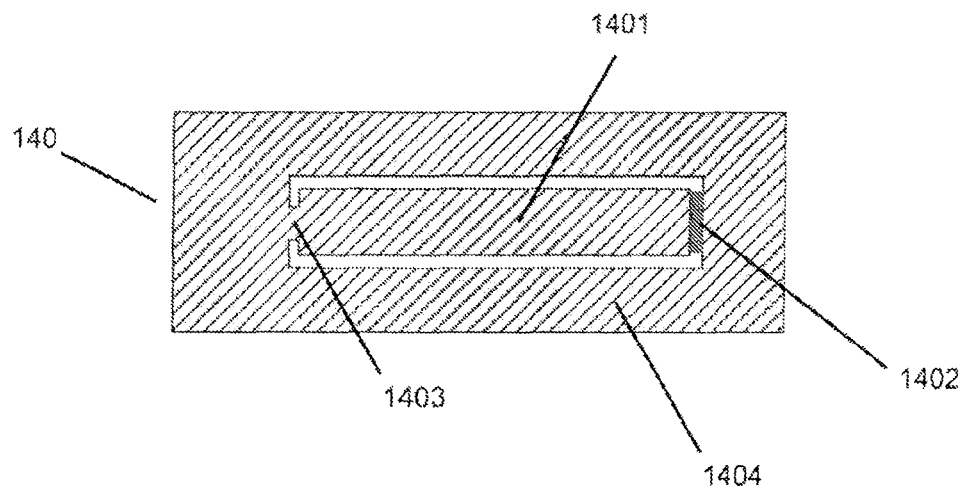
FIG. 14 is a plan view of a first embodiment of the lever and lever return springs of a mechanical driver according to the present invention.
Figure 15:
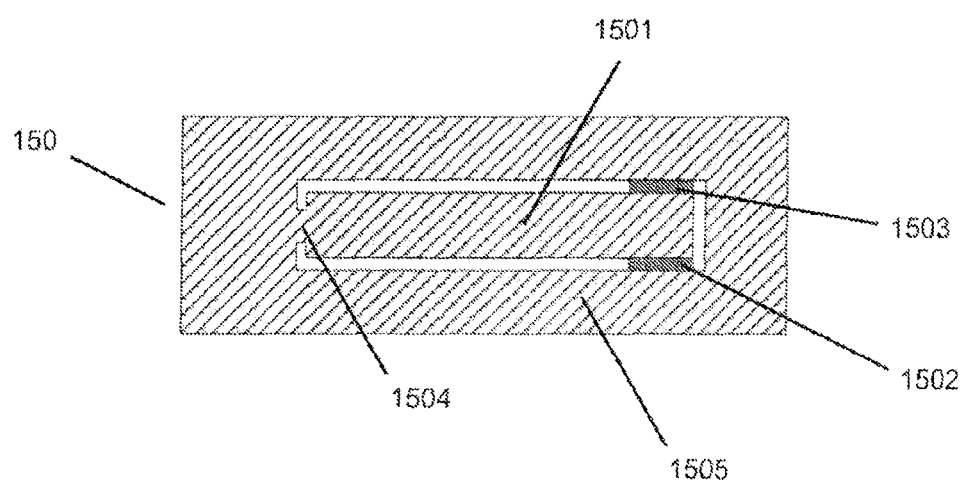
FIG. 15 is a plan view of a second embodiment of the lever and lever return springs of a mechanical driver according to the present invention.

FIGS. 14 and 15 show the addition of a return spring to the lever described in FIGS. 4 and 5. The return spring acts to return the lever to its initial position and to keep the movable end of the lever in constant contact with the wedge shaped member. In FIG. 14 the return spring 1402 is formed such that on end is connected to the lever 1401 and the other end is connected to the frame 1404. FIG. 14 shows the return spring 1402 fixed to the end of the lever 1401 able to rotate about the pivot point 1403.

FIG. 15 shows an alternative embodiment of the return spring for the lever. The return spring 1502 and 1503 is attached at one end to the side of the lever 1501 and at the other end to the frame 1505. It will be apparent to those skilled in the art that there are other suitable arrangements for the return spring. The lever 1501 is rotatable about the pivot point 1054.

In preferred embodiment the return spring 1402, 1502 and 1503 is formed from an elastomeric material such as silicone or rubber. In a preferred embodiment the return spring 1402, 1502 and 1503 is formed by injection molding or casting the elastomeric material. In a further preferred embodiment the return spring 1402, 1502 and 1503 is formed by casting the elastomeric material and then curing the material with radiation. In a further preferred embodiment the elastomeric material is injection molded or cast in situ and to fix the return spring 1402, 1502 and 1503 to the lever 1401 and 1501 and to the frame 1404 and 1505. A number of elastomeric materials are suitable for this purpose including self adhesive liquid silicone preparations for injection molding such as Elastosil LR 3071 and Silpuran 6700 (Wacker Chemie AG, München, Germany) and self adhesive liquid silicone preparations for casting and ultra violet light curing such as Loctite Nuva-Sil Silicone (Henkel AG & Co. KGaA, Dusseldorf, Germany) and Novaguard RTV 800-305 (NovaGuard, Clevland, Ohio, USA). It is preferred that the material used in the fabrication of the frame 105 is the same as the material chosen for the wedge shaped member 102. This would simplify the manufacturing process and could allow the manufacture of the wedge shaped member 102 and the frame 105 in a single process such as an injection molding step.

The lever 1401 and 1501 is made from a polymer that provides the appropriate mechanical properties and resists wear from the movement of the wedge shaped member and the piston. It is preferred that the material also has a low coefficient of friction. Materials such as polyether ether ketone (PEEK), Grivory and polycarbonate and polyacrylate are all suitable materials for the lever 1401 and 1501. Those skilled in the art will recognise other appropriate materials for the lever 1401 and 1501. The lever 1401 and 1501 can be fabricated using polymer injection molding or polymer casting techniques. Other methods for fabricating the lever 1401 and 1501 are known to those skilled in the art. It is preferred that the fabrication technique used for forming the lever 1401 and 1501 can produce parts with an accuracy of better than +/−20 microns. It is also preferred that the techniques chosen to fabricate the lever 1401 and 1501 can produce large numbers of parts, quickly and cost effectively. It is preferred that the material used in the fabrication of the frame 1404 and 1505 is the same as the material chosen for the lever 1401 and 1501. This would simplify the manufacturing process and could allow the manufacture of the lever 1401 and 1501 and the frame 1404 and 1505 in a single process such as an injection molding step.

In FIG. 14 and FIG. 15 there is described a lever 1401 and 1501 respectively where one end of the lever is fixed to the frame 1404 and 1505 respectively by a pivot point 1404 and 1504 respectively. In a preferred embodiment the pivot point 1404 and 1504 can be formed by removing material from the lever 1401 and 1501 in this part of the device to allow the lever to bend and for the bending to be essentially restricted to the pivot point 1404 and 1504. It will be appreciated by those skilled in the art that alternative pivot point structures can be used.

It will be appreciated by those skilled in the art that the embodiments of the lever shown in FIGS. 14 and 15 can be incorporated into other embodiments of the mechanical driver according to the present invention.

FIGS. 16, 17, 18 and 19 show alternative arrangements for a return spring for the piston. The return spring acts to return the piston to its initial position (its first position) and to hold the piston in constant contact with the lever or the wedge shaped member in the embodiments of the present invention. FIG. 16 shows a return spring 1603 formed between the perimeter of an opening in the frame 1602 and the perimeter of the piston 1601. FIG. 17 shows a return spring 1703 formed between the perimeter of an opening in the frame 1702 and the surface and perimeter of the piston 1601. FIG. 18 shows a return spring 1803 formed on one face of the frame 1802 and the perimeter of the piston 1801. FIG. 19 shows a return spring 1903 formed on one face of the frame 190 and the surface and perimeter of the piston 1901.

In preferred embodiment the return spring for the piston 1601, 1701, 1801 and 1901 is formed from an elastomeric material such as silicone or rubber. In a preferred embodiment the return spring for the piston 1601, 1701, 1801 and 1901 is formed by injection molding or casting the elastomeric material. In a further preferred embodiment the return spring for the piston 1601, 1701, 1801 and 1901 is formed by casting the elastomeric material and then curing the material with radiation. In a further preferred embodiment the elastomeric material is injection molded or cast in situ and to fix the return spring for the piston 1601, 1701, 1801 and 1901 to the piston 1601, 1701, 1801 and 1901 and to the frame 1602, 1702, 1802 and 1902. A number of elastomeric materials are suitable for this purpose including self adhesive liquid silicone preparations for injection molding such as Elastosil LR 3071 and Silpuran 6700 (Wacker Chemie AG, München, Germany) and self adhesive liquid silicone preparations for casting and ultra violet light curing such as Loctite Nuva-Sil Silicone (Henkel AG & Co. KGaA, Dusseldorf, Germany) and Novaguard RTV 800-305 (NovaGuard, Clevland, Ohio, USA). It is preferred that the material used in the fabrication of the frame 1602, 1702, 1802 and 1902 is the same as the material chosen for the piston 1601, 1701, 1801 and 1901. This would simplify the manufacturing process and could allow the manufacture of the piston 1601, 1701, 1801 and 1901 and the frame 1602, 1702, 1802 and 1902 in a single process such as an injection molding step.

It will be apparent to those skilled in the art that the arrangements for a return spring for the piston described in FIGS. 16, 17, 18 and 19 can be incorporated in to other embodiments of the mechanical driver according to the present invention, such as the described first, second, third, fourth and fifth embodiments of the mechanical driver.

In a preferred embodiment the return spring for the piston can form the pumping membrane of a micro pump.

FIG. 20 describes a fifth embodiment of the mechanical driver according to the present invention. The elements of the fifth embodiment of the mechanical driver according to the present invention are essentially similar to the element described in the third embodiment of the mechanical driver according to the present invention in FIG. 6. The elements of the fifth embodiment of the mechanical driver according to the present invention are arranged so that when in the inactive state the return springs 2004, 2007 and 2005 are placed under tension when the device is assembled. Tensioning of the return spring 2004 ensures that the piston 2001 is constantly in contact with the lever 2004 and ensures that any movement in the lever 2004 moves the piston 2001. This increases the accuracy and repeatability of the action of the mechanical driver. Tensioning of the return spring 2007 ensures that the lever 2004 is constantly in contact with the angled surface of the wedge shaped member 2002 and ensures that movement of the wedge shaped member 2002 moves the lever 2004. This further increases the accuracy and repeatability of the action of the mechanical driver. Tensioning of the return spring 2005 ensures that the shape memory alloy 2003 is held in tension and ensures that the contraction of the shape memory alloy 2003 moves the shape memory alloy 2003. This further increases the accuracy and repeatability of the action of the device. FIG. 20 shows the fifth embodiment of the present invention in the start position. The wedge shaped member 2002, the lever 2004 and the piston 2001 are in the first position. The shape memory alloy 2003 is elongated and the return springs 2004, 2005 and 2007 are at their respective first tension points. Furthermore, the frame 2006 of the mechanical driver 200 is shown.

FIG. 21 shows the fifth embodiment of the mechanical driver according to the present invention in an activated state and is similar to the activated state described with reference to the third embodiment of the mechanical driver according to the present invention. The piston 2101, the return springs 2104, 2105, 2107, the wedge shaped member 2102, the shape memory alloy 2103, the lever 2104, and the frame 2106 of the mechanical driver 210 are shown.

An example of the application of the miniaturised mechanical driver according to the mechanical driver according to the present invention is as a micro-pump as shown in FIG. 22. The micro-pump 220 has a pumping chamber 2207 with fluidic connection via an inlet valve 2208 to a reservoir 2211. At least part of the pumping chamber wall is flexible, and in a preferred embodiment the piston 2204 of the miniature mechanical driver is fixed to the flexible portion of the pumping chamber wall. In a preferred embodiment the flexible portion of the pumping chamber 2207 wall forms the return spring for the piston 2204 as described with reference to FIGS. 16, 17, 18 and 19. Heating of the shape memory alloy 2202 causes the shape memory alloy 2202 to contract and displace the wedge shaped member 2201 from its first position to its second position. This causes the return spring 2205 on the wedge shaped member 2201 to be stretched from its first position to its second position. The movement of the wedge shaped member 2201 also displaces the lever 2203 from its first position to its second position and the lever 2203 displaces the piston 2204 from its first position to its second position. The lever 2023 is connected to the frame via a return spring 2212 and rotated about the fixed rotation point 2206. The movement of the piston 2204 from its first position to its second position causes the volume of the pumping chamber 2207 to decrease and forces the fluid out of the pumping chamber 2207 through outlet valve 2209. Allowing the shape memory alloy 2202 to cool causes the shape memory alloy 2202 to elongate to its starting length assisted by the contraction of the return spring 2205 on the wedge shaped member 2205 to its starting length. Movement of the wedges shaped member 2201 to its first position allows the lever 2203 to be returned to its first position by the action of the return spring 2212 on the lever 2203. The return of the lever 2203 to its first position allows the piston to be returned to its first position by the action of the return spring on the piston. The return of the piston 2204 to its first position increases the volume of the pumping chamber 2207 and allows fluid to enter the pumping chamber 2207 from the reservoir 2211 via the inlet valve 2208.

The inlet valve 2208 and outlet valve 2209 are one-way valves. The outlet valve 2209 opens when the pressure in the pumping chamber 2207 increases when the piston 2204 is moved from its first position to its second position and the volume of the pumping chamber 2207 decreases. The inlet valve 2208 closes when the pressure in the pumping chamber increases. When the pumping chamber is filled with fluid, fluid is selectively forced through the outlet valve when the piston moves for its first position to its second position. The inlet valve opens when the pressure in the pumping chamber 2207 decreases as the piston 2204 returns from its second position to its first position and the volume of the pumping chamber 2207 increases. The outlet valve 2209 closes when the pressure in the pumping chamber decreases. Therefore, fluid is selectively drawn from the reservoir 2211 into the pumping chamber 2207 when the piston moves to its second position from its first position. Repeated operation of the of the micro-pump 220 causes fluid to be pumped from the reservoir 2211 to the outlet 2210. To assist the drawing of fluid from the reservoir 2211, the reservoir 2211 may be pressurised.

The micro-pump described with reference to FIG. 22 finds particular use in an infusion system for the infusion of therapeutic products.

The following clauses are offered as a further description of the mechanical driver, pump and infusion system according to the invention.

Clause 1

A miniature mechanical driver comprising:
a piston,
a wedge shaped member operatively coupled and in constant contact with the piston, and able to deflect the piston, and
a shape memory alloy operatively coupled to the wedge shaped member and able to move the wedge shaped member such that the wedge shaped member deflects the piston, the shape memory alloy is held at a predetermined tension in its start position.

Clause 2

A mechanical driver comprising:
a lever, able to rotate at a fixed point,
a wedge shaped member operatively coupled to and in constant contact with the lever at a point some distance from the fixed rotation point, and able to deflect the lever about the fixed rotation point,
a shape memory alloy operatively coupled to the wedge shaped member and able to move the wedge shaped member such that the wedge shaped member deflects the lever, the shape memory alloy is held at a predetermined tension in its start position, and
a piston drive point located on and in constant contact with the lever, some distance from the fixed rotation point of the lever.

Clause 3

Mechanical driver according to clause 1 or 2, wherein the wedge shaped member has a single angled surface operatively coupled to the piston or the lever.

Clause 4

Mechanical driver according to clause 1 or 2, wherein the wedge shaped member has two angled surfaces operatively coupled to the piston or the lever.

Clause 5

Mechanical driver according to clause 3 or 4, wherein the wedge shaped member has surfaces at either end of each angled surface that are essentially planar to the direction of travel of the wedge shaped member and that are in contact with the piston or the lever when the wedge shaped member is in its first and second positions respectively.

Clause 6

Mechanical driver according to any of the preceding clauses, wherein the wedge shaped member is attached to a frame by flexible tethers.

Clause 7

Mechanical driver according to any of the preceding clauses, wherein the shape memory alloy is a wire.

Clause 8

Mechanical driver according to clause 7, wherein the shape memory wire is fixed at one end to the wedge shaped member.

Clause 9

Mechanical driver according to clause 7 or 8, wherein the shape memory wire is looped around at least part of the wedge shaped member and the ends of the shape memory wire are attached to fixed points.

Clause 10

Mechanical driver according to any of the clauses 2-9, wherein the piston drive point is located relative to the fixed rotation point of the lever and the coupling point of the wedge shaped member with the lever so as to optimise the accuracy of movement of the piston.

Clause 11

Mechanical driver according to any of the preceding clauses, further comprising a return spring operatively coupled to the wedge shaped member, and acting against the force of the shape memory alloy.

Clause 12

Mechanical driver according to clause 11, wherein the return spring is an elastomeric material.

Clause 13

Mechanical driver according to clause 11 or 12, wherein the return spring is fabricated using an injection molding or casting technique.

Clause 14

Mechanical driver according to any of the preceding clauses, further comprising a return spring operatively coupled to the piston, and acting to return the piston to its starting position.

Clause 15

Mechanical driver according to clause 14, wherein the return spring on the piston is biased when the piston is in its starting position.

Clause 16

Mechanical driver according to clause 14 or 15, wherein the return spring forms the pumping membrane of a micro pump.

Clause 17

Mechanical driver according to any of the clauses 14-16, wherein the return spring is an elastomeric material.

Clause 18

Mechanical driver according to clause 17, wherein the return spring is fabricated using an injection molding or casting technique.

Clause 19

Mechanical driver according to any of the preceding clauses, further comprising a return spring operatively coupled to the lever, and acting to return the lever to its starting position.

Clause 20

Mechanical driver according to clause 19, wherein the return spring on the lever is biased when the lever is in its starting position.

Clause 21

Mechanical driver according to clause 19 or 20, wherein the return spring is an elastomeric material.

Clause 22

Mechanical driver according to clause 21, wherein the return spring is fabricated using an injection molding or casting technique.

Clause 23

A pump comprising the miniature mechanical driver according to any preceding clause.

Clause 24

Pump according to clause 23 for pumping liquid therapeutic product comprising a pumping chamber having an inlet valve and an outlet valve wherein a volume of the pumping chamber is caused to change by actuation of the miniature mechanical driver.

Clause 25

An infusion system including the pump of any of clauses 23 and 24. It will be apparent to those skilled in the art that various modifications of the present invention are envisaged without departing from the scope of the invention, which is defined by the appending claims.

The invention claimed is:

1. A mechanical driver comprising:
   a piston;
   a wedge shaped member operatively coupled and in constant contact with the piston and moveable relative to the piston; and
   a shape memory alloy operatively coupled to the wedge shaped member to move the wedge shaped member relative to the piston such that the wedge shaped member deflects the piston;
   wherein the shape memory alloy is held at a predetermined tension in its start position; and
   wherein the wedge shaped member is arranged so that it moves only in a substantially linear direction relative to the piston while the wedge shaped member is operatively coupled and in constant contact with the piston.

2. The mechanical driver according to claim 1, wherein the wedge shaped member has a single angled surface.

3. The mechanical driver according to claim 2, wherein the angled surface is an inclined straight surface.

4. The mechanical driver according to claim 1, wherein the wedge shaped member has two angled surfaces.

5. The mechanical driver according to claim 4, wherein the angled surfaces are two opposite inclined straight surfaces.

6. The mechanical driver according to claim 2,
   wherein the single angled surface has a first end and a second end;
   wherein the wedge shaped member has a first flat surface and a second flat surface; and
   wherein the first flat surface is adjacent to the first end and the second flat surface is adjacent to the second end, and the first and second flat surfaces are essentially planar to the direction of travel of the wedge shaped member.

7. The mechanical driver according to claim 6, wherein the wedge shaped member is movable from the start position into a second position, and vice versa, and the piston is in contact with the first flat surface when the wedge shaped member is in the start position and the piston is in contact with the second flat surface when the wedge shaped member is in the second position.

8. The mechanical driver according to claim 1, wherein the wedge shaped member is attached to a frame by flexible tethers.

9. The mechanical driver according to claim 1, wherein the shape memory alloy is a wire.

10. The mechanical driver according to claim 9, wherein the shape memory wire is fixed at one end to the wedge shaped member.

11. The mechanical driver according to claim 9, wherein the shape memory wire is looped around at least part of the wedge shaped member and ends of the shape memory wire are attached to fixed points.

12. The mechanical driver according to claim 1, wherein the mechanical driver further comprises a return spring operatively coupled to the wedge shaped member, and acting against a force of the shape memory alloy.

13. The mechanical driver according to claim 12, wherein the return spring is an elastomeric material.

14. The mechanical driver according to claim 12, wherein the return spring is fabricated using an injection molding or casting technique.

15. The mechanical driver according to claim 1, wherein the mechanical driver further comprises a return spring operatively coupled to the piston, and acting to return the piston to its starting position.

16. The mechanical driver according to claim 15, wherein the return spring is biased when the piston is in its starting position.

17. The mechanical driver according to claim 15, wherein the return spring is an elastomeric material.

18. The mechanical driver according to claim 17, wherein the return spring is fabricated using an injection molding or casting technique.

19. A pump comprising the mechanical driver according to claim 1.

20. The pump according to claim 19 for pumping a liquid therapeutic product comprising a pumping chamber having an inlet valve and an outlet valve, wherein a volume of the pumping chamber is caused to change by actuation of the mechanical driver.

21. An infusion system including the pump according to claim 19.

22. A mechanical driver comprising:
- a piston;
- a wedge shaped member operatively coupled and in constant contact with the piston and moveable relative to the piston;
- a shape memory alloy operatively coupled to the wedge shaped member to move the wedge shaped member relative to the piston such that the wedge shaped member deflects the piston, wherein the shape memory alloy is held at a predetermined tension in its start position; and
- a return spring operatively coupled to the piston, and acting to return the piston to its starting position;
- wherein the return spring forms a pumping membrane of a micro pump.

* * * * *